(12) United States Patent
Bowers et al.

(10) Patent No.: US 6,405,560 B2
(45) Date of Patent: Jun. 18, 2002

(54) APPARATUS FOR ANALYSIS OF IMPURITIES IN LIQUID CARBON DIOXIDE

(75) Inventors: Charles W. Bowers, Livermore; Wilfried Krone-Schmidt, Fullerton, both of CA (US)

(73) Assignee: Eco-Snow Systems, Inc., Livermore, CA (US)

( * ) Notice: Subject to any disclaimer, the term of this patent is extended or adjusted under 35 U.S.C. 154(b) by 0 days.

(21) Appl. No.: 09/886,098

(22) Filed: Jun. 22, 2001

Related U.S. Application Data

(63) Continuation of application No. 09/411,396, filed on Oct. 4, 1999, now Pat. No. 6,276,169.

(51) Int. Cl.[7] ................................................. F25J 1/00
(52) U.S. Cl. ............................................. 62/603; 62/617
(58) Field of Search ................................... 62/603, 617

(56) References Cited

U.S. PATENT DOCUMENTS

| | | | | |
|---|---|---|---|---|
| 3,124,442 A | * | 3/1964 | Rich ............................ | 62/602 |
| 4,337,071 A | * | 6/1982 | Yang ........................... | 62/600 |
| 5,566,553 A | * | 10/1996 | Gibot et al. ................... | 62/603 |
| 5,868,003 A | * | 2/1999 | Simas et al. .................... | 62/603 |
| 6,023,941 A | * | 2/2000 | Rhoades ....................... | 62/603 |
| 6,116,049 A | * | 9/2000 | Filipczak ...................... | 62/603 |

* cited by examiner

*Primary Examiner*—Ronald Capossela
(74) *Attorney, Agent, or Firm*—R. Craig Armstrong

(57) ABSTRACT

Liquid $CO_2$ is expanded in specially designed primary and secondary nozzles to produce frozen solid $CO_2$. The impurities initially contained in the liquid $CO_2$ are trapped inside of the frozen $CO_2$, which is collected in a clean container. The container is emptied on top of a high purity surface. The impurities are concentrated on the surface, since these impurities are non-volatile and do not escape with the $CO_2$ gas formed as the frozen $CO_2$ is heated by the ambient temperature to its sublimation point. After all of the frozen $CO_2$ has sublimed, the surface can be analysed by standard analysis methods to determine quantity and composition of the impurities. The determination and quantification of non-volatile impurities, such as organic oils and greases, in the $CO_2$ supply that feeds, for example, cleaning systems utilizing $CO_2$, is thus made possible.

10 Claims, 2 Drawing Sheets

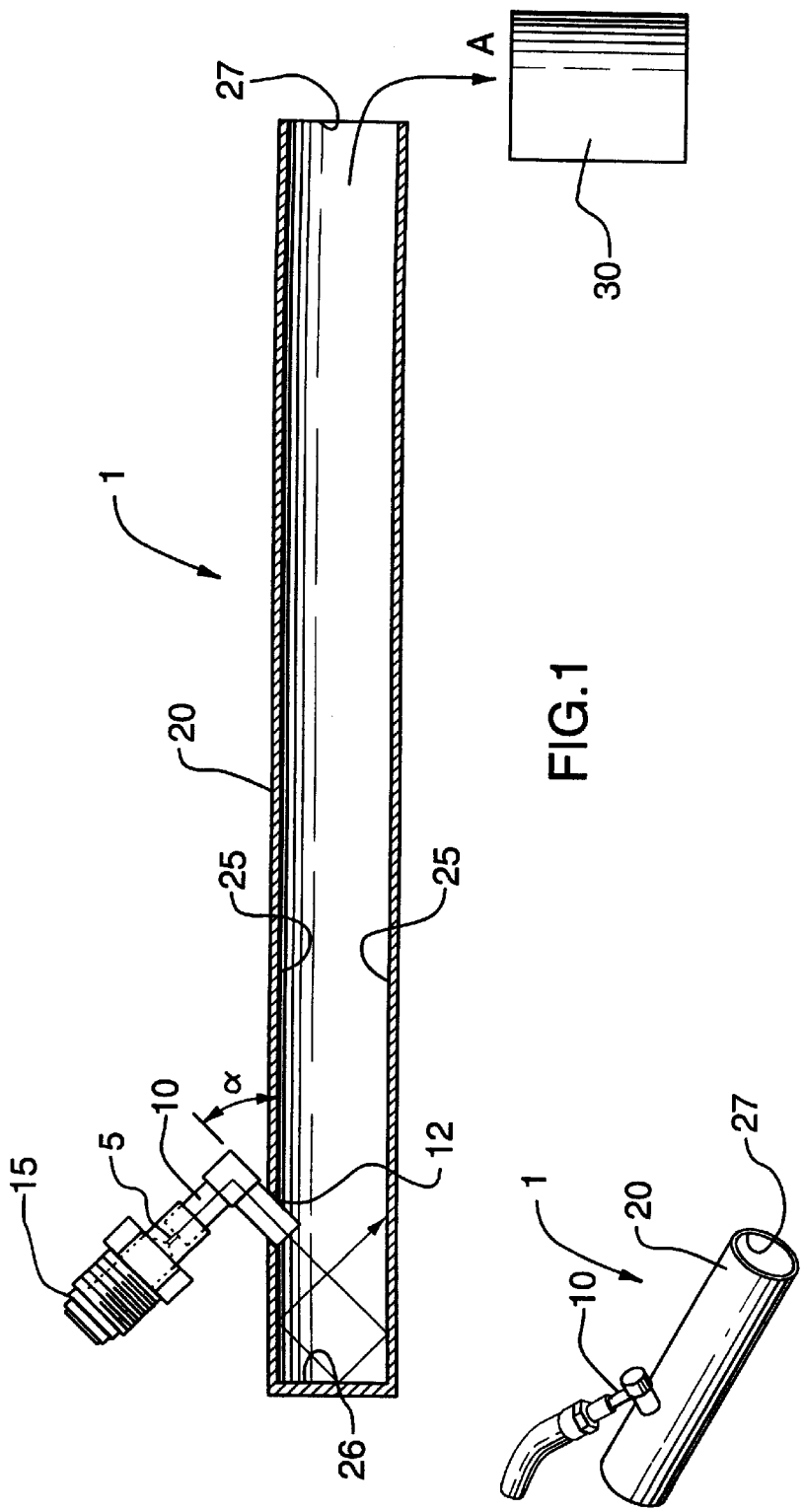

APPARATUS FOR ANALYSIS OF IMPURITIES IN LIQUID CARBON DIOXIDE

REFERENCE TO RELATED APPLICATION

This is a continuation of application Ser. No. 09/411,396, filed Oct. 4, 1999 now U.S. Pat. No. 6,276,169.

BACKGROUND OF THE INVENTION

1. Field of the Invention

This invention relates to an apparatus for analysing impurity levels in liquid carbon dioxide ($CO_2$).

2. Description of the Prior Art

Previous methods of separating impurities from liquid $CO_2$ rely primarily on High Pressure Liquid Chromatography (HPLC) to separate out the constituents of impurities contained in the liquid $CO_2$, for analysis of the impurity levels. The equipment necessary to carry out these methods is expensive and has an inherent lower resolution, quantification, and accuracy than that which is required for many applications. Also, some impurities may not be able to be separated using this technique, rendering the HPLC method useless for detecting the presence of these impurities. Furthermore, the equipment has to be calibrated frequently, usually just prior to use.

SUMMARY OF THE INVENTION

It is an object of the invention to mitigate and/or obviate the drawbacks of the prior art mentioned above, and provide an easy to use and inexpensive apparatus for determining the impurity levels in liquid $CO_2$.

In the invention, $CO_2$ snow (frozen $CO_2$) is used as a medium to determine non-volatile impurities in the $CO_2$ snow, and consequently determine the purity of the liquid $CO_2$. Liquid $CO_2$ is expanded in specially designed primary and secondary nozzles to produce low-density and low-velocity $CO_2$ snow. The impurities initially contained in the liquid $CO_2$ are trapped inside of the frozen $CO_2$, which is preferably collected in a clean container. According to one preferred embodiment, the container is emptied on top of a high purity surface. The impurities are concentrated on the surface, since these impurities are non-volatile and do not escape with the $CO_2$ gas formed as the $CO_2$ snow is heated by the ambient temperature to its sublimation point. After all of the $CO_2$ snow has sublimed, the surface can be analysed by standard methods to determine quantity and composition of the impurities. The determination and quantification of non-volatile impurities, such as organic oils and greases, in the $CO_2$ supply that feeds, for example, cleaning systems utilizing liquid $CO_2$, is thus made possible.

The system according to the invention has a primary nozzle and a secondary nozzle. The primary nozzle is connected to a liquid $CO_2$ source via one or more small orifices having a suitable shape, for example substantially round, a slit or an annulus shape (an annular slit). Liquid $CO_2$ is expanded after the orifices, and the expansion causes the liquid to freeze into snow particles. The primary nozzle is arranged to project the snow particles at a certain angle into the secondary nozzle. The snow particles collide with each other and the walls of the secondary nozzle, and secondary nozzle geometry is designed to cause the snow to have multiple collisions with these walls. The collisions reduce the velocity of the snow and cause many snow particles to stick together further reducing the snow velocity. Thus, the snow is easily collected in a container for analysis. The container is emptied onto a high purity surface, and as the snow sublimes from the surface, the non-volatile impurities remain on the surface and accumulate in high concentrations.

The advantage of this system is the simplicity of use and low cost, since it does not require expensive analytical equipment. This simple and inexpensive method enables part-per-billion (ppb) resolution of non-volatile impurities.

Further features of the invention will be described or will become apparent in the course of the following detailed description.

BRIEF DESCRIPTION OF THE DRAWINGS

In order that the invention may be more clearly understood, the preferred embodiment thereof will now be described in detail by way of example, with reference to the accompanying drawing, in which:

FIG. 1 is a schematic side view of a system according to the invention,

FIG. 2 is a schematic elevational side view of the system shown in FIG. 1,

DETAILED DESCRIPTION OF THE PREFERRED EMBODIMENT

Figure 3B:
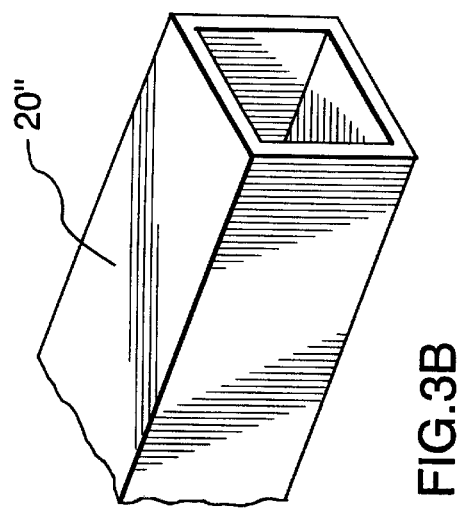
FIG. 3B is a schematic elevational side view of a second embodiment of the secondary nozzle.
Figure 3A:
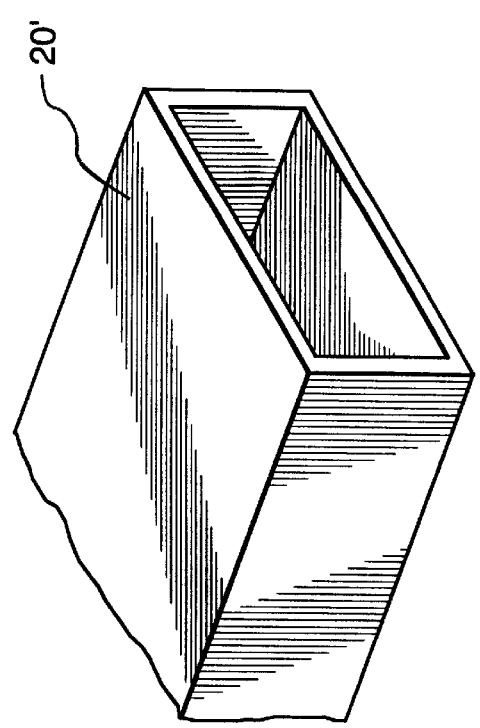
FIG. 3A is a schematic elevational side view of a first embodiment of the secondary nozzle.
Figure 3C:
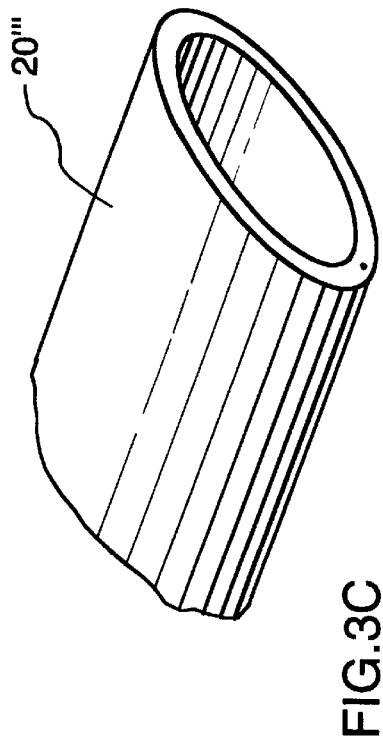
FIG. 3C is a schematic elevational side view of a third embodiment of the secondary nozzle.

As shown in FIGS. 1 and 2, the system 1 according to the invention has a primary nozzle 10 and a secondary nozzle 20. The primary nozzle 10 has one or more small orifices 5 arranged upstream of the primary nozzle, and is connected to a liquid $CO_2$ source (not shown) via a valve (not shown). The orifices are of suitable shape for example substantially round, a slit or an annulus shape (an annular slit). A fitting 15, for example a VCR fitting, is arranged between the primary nozzle 10 and the liquid $CO_2$ source. Liquid $CO_2$ is expanded in the orifices 5, and the expansion causes the liquid to freeze into snow particles. The primary nozzle 10 is mounted to the secondary nozzle via a sealed opening 12 and is arranged to project the snow particles at a certain angle a into the secondary nozzle 20. The secondary nozzle has side walls 25, a bottom wall 26 and a discharge opening 27. The side walls form a closed cross-section and the bottom wall is sealingly fastened to one end of the side walls. Alternatively, the secondary nozzle 20 is fabricated from a solid piece of material, for example by milling and drilling. The snow particles collide with each other, and the side and bottom walls of the secondary nozzle 20. The secondary nozzle geometry is designed to cause the snow particles to have multiple collisions with the walls, examples of preferred embodiments are shown in FIGS. 3A to 3C. The collisions reduce the velocity of the snow and cause many snow particles to stick together, further reducing the snow velocity. The angle α is chosen so that a maximum number of collisions is obtained without clogging the secondary nozzle with frozen $CO_2$. A preferred angle is 45 degrees, but any angle between 1 and 89 degrees may be used. The cross-section of the secondary nozzle 20 is circular, oval, rectangular, quadratic or any geometry which will provide the necessary collisions. Thus, the snow is easily discharged through the discharge opening 27 and collected in a collection means 30 for analysis. The collection means is any suitable container, which can hold the frozen $CO_2$ without spilling or contaminating it. The collected snow is preferably deposited onto a clean surface (not shown) and, as the snow sublimes off the surface, the non-volatile impurities remain on the surface and accumulate in high concentrations.

The invention thus uses $CO_2$ snow as a medium to determine non-volatile impurities in $CO_2$ snow, and consequently determine the purity of liquid $CO_2$.

Since each of the primary and secondary nozzles are of fixed mechanical dimensions they can be calibrated to measure only one property, either mass loss of the bulk material or collection time, and a second measurement of the weight of the accumulated impurity or volume and density can then be used to calculate the exact concentration of impurities.

The method used by the invention preferably includes the steps of connecting a liquid $CO_2$ supply to the primary nozzle, expanding liquid $CO_2$ in the primary nozzle to produce frozen solid $CO_2$, which is projected further into the secondary nozzle, to produce low-density and low-velocity $CO_2$ snow; the impurities initially contained in the liquid $CO_2$ are trapped inside of the frozen $CO_2$, collecting the $CO_2$ snow in a collecting means, which is any suitable clean container, such as a glass beaker, preferably emptying the container, after collecting a sufficient quantity, onto a high purity surface, such as a polished silicon wafer, leaving the impurities concentrated on the wafer, since these impurities are non-volatile and do not escape with the $CO_2$ gas analysing the surface by standard methods, after all of the $CO_2$ snow has sublimed, to determine quantity and composition of the impurity.

Alternatively, the frozen $CO_2$ from the secondary nozzle 20 may be led directly to a realtime analysis means (not shown), for direct analysis. The primary nozzle 10, the secondary nozzle 20 and the real-time analysis means are preferably assembled as one unit, to facilitate field use.

Thus, the determination and quantification of non-volatile impurities, such as organic oils and greases, in the $CO_2$ supply that feeds, for example, cleaning systems utilizing liquid $CO_2$, is made possible. The user of the system according to the invention can easily verify the purity of the $CO_2$ prior to using it for cleaning operations.

Example

A $CO_2$ cylinder, which was known to contain an impurity, was weighed, the analysis nozzles (primary nozzle and secondary nozzle) connected to it and 2 pounds of liquid $CO_2$ were expanded through the nozzle. A 1 liter beaker was filled with snow, inverted onto a Si wafer, and the snow was allowed to sublime.

The resulting, highly visible layer was then analysed by ellypsometry and weighing.

Four spots on the wafer were chosen for ellipsometer analysis: the centre, halfway to the edge, a thicker hazy spot and one spot near the edge. The thickness were recorded as follows: 141 Å, 163 Å, 260 Å, and 220 Å, respectively. On first order, the average of these values gives 196 Å±54 Å.

The total contaminated area can be calculated from the diameter of about 3.5" or 9 cm, equalling 64 $cm^2$. The volume of this material is then 196×10−8 cm times 64 $cm^2$ equalling 1.25×10−4 $cm^3$. Assuming a density of 0.8 g/ml for organic oils gives 1×10−4 g, or 0.1 mg.

The wafer was then weighed on a balance, rinsed with acetone, and weighed again; the net weight was 0.2 mg+0−0.1 mg. This contaminant was collected from 2 pounds of liquid $CO_2$. Thus, we can calculate 1×10−4 g divided by 1000 g equals 1×10−7, or 100 ppb.

Both methods calculated an impurity level of 100 ppb. Based on this and similar results, it is believed that contamination levels of less than 10 ppb can be visually detected and with appropriate instrumentation quantified. The procedure may be repeated multiple times to give yet higher degrees of resolution.

It will be appreciated that the above description relates to the preferred embodiment by way of example only. Many variations on the invention will be obvious to those knowledgeable in the field, and such obvious variations are within the scope of the invention as described and claimed, whether or not expressly described.

For example, contamination concentrated in the above described way, may be further analysed by standard analysis methods like Fourier Transform Infrared Spectroscopy (FTIR), Mass Spectrometry, Gas Chromatography ("HPGC"), Residual Gas Analysis (RGA), film thickness measurements etc., to determine the exact nature and proportions of the impurity.

What is claimed as the invention is:

1. An apparatus for separation of non-volatile impurities from liquid carbon dioxide, said apparatus comprising:

a primary nozzle, connected to a liquid $CO_2$ source, at least one small orifice, arranged in a first conduit upstream of said primary nozzle, and arranged to expand said liquid $CO_2$ in said primary nozzle to form frozen solid $CO_2$, a secondary nozzle arranged so that said first nozzle projects said frozen solid $CO_2$ at an acute angle into said secondary nozzle; and a collection means, positioned to receive said frozen $CO_2$, from a discharge opening of said secondary nozzle;

wherein said secondary nozzle has side walls, forming a closed cross-section, and a bottom wall, sealingly attached to one end of said side walls, and wherein said primary nozzle is mounted to said secondary nozzle via a sealed opening and is arranged to project the frozen $CO_2$ at a preset angle into said secondary nozzle, to cause the frozen $CO_2$ to collide with said walls and said bottom wall to lower the velocity of the individual particles of the frozen $CO_2$.

2. An apparatus according to claim 1, wherein said primary nozzle is connected to said liquid $CO_2$ source via said first conduit, said first conduit having a valve, which may be opened or closed to permit or restrict the flow of $CO_2$ through said first conduit.

3. An apparatus according to claim 2, wherein said preset angle is approximately 45 degrees.

4. An apparatus according to claim 1, wherein said preset angle is approximately 45 degrees.

5. An apparatus according to claim 1, wherein said closed cross-section is rectangular.

6. An apparatus according to claim 5, wherein said preset angle is approximately 45 degrees.

7. An apparatus according to claim 1, wherein said closed cross-section is square.

8. An apparatus according to claim 7, wherein said preset angle is approximately 45 degrees.

9. An apparatus according to claim 1, wherein said closed cross-section is oval.

10. An apparatus according to claim 9, wherein said preset angle is approximately 45 degrees.

* * * * *